United States Patent
Meron et al.

(10) Patent No.: US 7,119,814 B2
(45) Date of Patent: *Oct. 10, 2006

(54) SYSTEM AND METHOD FOR ANNOTATION ON A MOVING IMAGE

(75) Inventors: Gavriel Meron, Petach Tikva (IL); Arkady Glukhovsky, Nesher (IL)

(73) Assignee: Given Imaging Ltd., Yoqneam (IL)

( * ) Notice: Subject to any disclaimer, the term of this patent is extended or adjusted under 35 U.S.C. 154(b) by 96 days.

This patent is subject to a terminal disclaimer.

(21) Appl. No.: 10/150,019

(22) Filed: May 20, 2002

(65) Prior Publication Data

US 2002/0171669 A1    Nov. 21, 2002

Related U.S. Application Data

(60) Provisional application No. 60/291,632, filed on May 18, 2001.

(51) Int. Cl.
- *G09G 5/00* (2006.01)
- *A61B 1/04* (2006.01)
- *G06K 9/36* (2006.01)

(52) U.S. Cl. .................. 345/619; 600/109; 600/424; 382/128; 382/286

(58) Field of Classification Search ............. 345/619, 345/440; 715/500.1, 853; 600/427, 523, 600/109, 309, 424, 300; 607/30, 28; 709/236; 705/3; 382/107, 128

See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,008,712 A | 2/1977 | Nyboer | |
| 4,278,077 A | 7/1981 | Mizumoto | |
| 4,689,621 A | 8/1987 | Kleinberg | |
| 4,741,327 A | 5/1988 | Yabe | |
| 4,844,076 A | 7/1989 | Lesho et al. | |
| 5,279,607 A | 1/1994 | Schentag et al. | |
| 5,604,531 A * | 2/1997 | Iddan et al. | 348/76 |
| 5,740,267 A * | 4/1998 | Echerer et al. | 382/132 |
| 5,749,908 A * | 5/1998 | Snell | 607/30 |
| 5,761,655 A * | 6/1998 | Hoffman | 707/4 |
| 5,819,736 A | 10/1998 | Avny et al. | |
| 5,822,539 A * | 10/1998 | van Hoff | 709/236 |
| 5,838,313 A * | 11/1998 | Hou et al. | 715/500.1 |

(Continued)

FOREIGN PATENT DOCUMENTS

DE    34 40 177    5/1986

(Continued)

OTHER PUBLICATIONS

The Radio Pill, Rowlands, et al., British Communications and Electronics, Aug. 1960, pp. 598-601.

(Continued)

*Primary Examiner*—Kee M. Tung
*Assistant Examiner*—Jin-Cheng Wang
(74) *Attorney, Agent, or Firm*—Pearl Cohen Zedek Latzer, LLP

(57) ABSTRACT

A system and method allows for the annotation of an image stream, which may be produced by, for example, an ingestible capsule. A workstation accepts images acquired by the capsule and displays the images on a monitor as a moving image. A user inputs an annotation which corresponds to a portion of the moving image, and the annotation is recorded in a database associated with the selected portion. The annotation may include, for example, textual notes regarding the image portion. The annotations may be displayed at a later time.

20 Claims, 3 Drawing Sheets

U.S. PATENT DOCUMENTS

| | | | |
|---|---|---|---|
| 5,920,317 A * | 7/1999 | McDonald | 715/853 |
| 5,924,074 A * | 7/1999 | Evans | 705/3 |
| 6,124,864 A * | 9/2000 | Madden et al. | 345/473 |
| 6,192,266 B1 * | 2/2001 | Dupree et al. | 600/427 |
| 6,240,312 B1 | 5/2001 | Alfano et al. | |
| 6,346,940 B1 * | 2/2002 | Fukunaga | 345/427 |
| 6,389,311 B1 * | 5/2002 | Whayne et al. | 600/523 |
| 6,512,953 B1 * | 1/2003 | Florio et al. | 607/28 |
| 6,614,452 B1 * | 9/2003 | Cable | 715/764 |
| 6,632,175 B1 * | 10/2003 | Marshall | 600/309 |
| 6,675,352 B1 * | 1/2004 | Osaki et al. | 715/512 |
| 6,692,430 B1 | 2/2004 | Adler | |
| 6,709,387 B1 * | 3/2004 | Glukhovsky et al. | 600/109 |
| 7,009,634 B1 * | 3/2006 | Iddan et al. | 348/76 |
| 2001/0017649 A1 | 8/2001 | Yaron | |
| 2001/0051766 A1 | 12/2001 | Gazdzinski | |
| 2002/0021828 A1 * | 2/2002 | Papier et al. | |
| 2002/0093484 A1 * | 7/2002 | Skala et al. | |
| 2002/0107444 A1 * | 8/2002 | Adler | |
| 2002/0198439 A1 | 12/2002 | Mizuno | |
| 2003/0151661 A1 | 8/2003 | Davidson et al. | |
| 2003/0208107 A1 * | 11/2003 | Refael | |

FOREIGN PATENT DOCUMENTS

| | | |
|---|---|---|
| IL | WO 01/50941 | 7/2001 |
| JP | 57-45833 | 3/1982 |
| JP | HEI 3-289779 | 12/1991 |
| JP | 4109927 | 4/1992 |
| JP | HEI 4-109927 | 4/1992 |
| JP | HEI 4-180736 | 6/1992 |
| JP | 5015515 | 1/1993 |
| JP | 7289504 | 11/1995 |
| JP | 2001 137182 | 5/2001 |
| JP | 2001 224551 | 8/2001 |
| JP | 2001224553 | 8/2001 |
| WO | WO 92/21307 | 12/1992 |
| WO | WO 98/11816 | 3/1998 |
| WO | WO 01/08548 | 2/2001 |
| WO | WO 01/65995 | 9/2001 |
| WO | WO 02/067593 | 8/2002 |

OTHER PUBLICATIONS

Video Camera to "TAKE"—RF System lab, Dec. 25, 2001.

Wellesley company sends body monitors into space—Crum, Apr. 1998.

Wireless transmission of a color television moving image from the stomach using a miniature CCD camera, light source and microwave transmitter Swain CP, Gong F, Mills TN. Gastrointest Endosc 1997;45:AB40.

BBC News Online—Pill camera to 'broadcast from the gut', Feb. 21, 2000, www.news.bbc.co.uk.

Wang, et al., " Integrated Micro-Instrumentation for Dynamic Monitoring of the Gastro-Intestinal Tract", Presented at IEEE Instrumentation and Measurement Technology Conference, May 2002, Anchorage, Ak, USA, www.see.ed.ac.uk/Naa.publications.html.

* cited by examiner

SYSTEM AND METHOD FOR ANNOTATION ON A MOVING IMAGE

CROSS-REFERENCE TO RELATED APPLICATIONS

The present application claims priority from U.S. Provisional Application Ser. No. 60/291,632, filed May 18, 2001, which is hereby incorporated by reference.

FIELD OF THE INVENTION

The present invention relates to a method and system for allowing a moving image to be annotated.

BACKGROUND OF THE INVENTION

When viewing a moving image, for example a moving image which may be used for medical diagnosis, the viewer may desire to record comments regarding certain portions or frames, or may wish to "bookmark" certain portions or frames.

For example, an in vivo imager system which is carried by an ingestible capsule may be used to image lumens within a patient. The imager system captures and transmits, for example, images of the GI tract to an external recording device while the capsule passes through the GI lumen. Such an in vivo imaging system provides a platform from which moving or still images of a lumen may be viewed. Large numbers of images may be collected for viewing. For example, the images may be combined in sequence, and a moving image of, for example, 40 minutes in length, may be presented to the user. It would be desirable to enable a user to note significant details or portions of such a set of images.

Therefore, a need exists for a system or method which enables the viewer of a moving image to annotate or bookmark the image.

SUMMARY OF THE INVENTION

An exemplary embodiment of the present invention provides a system and method for annotating an image stream, the image stream preferably being produced by an in vivo imaging device such as an ingestible capsule. A workstation accepts acquired images and displays the images on a monitor as, for example, a moving image. A user inputs an annotation which corresponds to a portion of the moving image, the annotation is recorded in a database, and the annotation is associated with the selected portion. The annotation may include, for example, textual notes regarding the image portion. The annotations may be recalled or displayed at a later time.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers is and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. It will be appreciated that a variety of programming languages may be used to implement the teachings of the invention as described herein.

Figure 1:
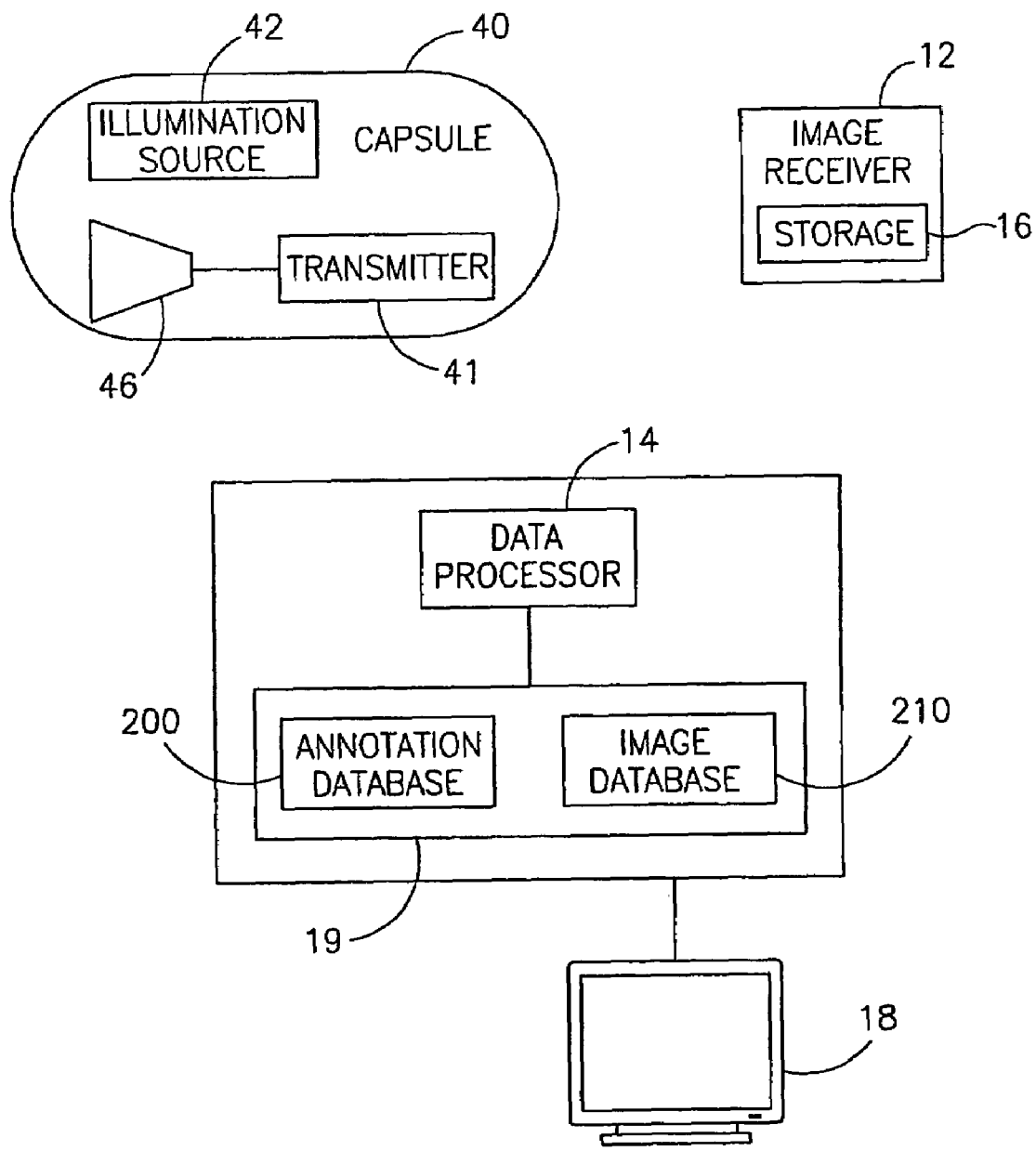
FIG. 1 shows a schematic diagram of an in vivo imaging system according to one embodiment of the present invention.

Reference is made to FIG. 1, which shows a schematic diagram of an in vivo imaging system according to one embodiment of the present invention. In an exemplary embodiment, the system comprises a capsule 40 having an imager 46, for capturing images, an illumination source 42, for illuminating the body lumen, and a transmitter 41, for transmitting image and possibly other information to a receiving device. An optical system (not shown), including, for example, lenses or mirrors, may aid in focusing reflected light onto the imager 46. The capsule 40 is swallowed by a patient and preferably traverses the patient's GI tract. In certain embodiments, the capsule and image capture system are similar to embodiments described in U.S. Pat. No. 5,604,531 or in WO 01/65995, both assigned to the common assignee of the present application. In alternate embodiments, other capsules or other image capture devices, and other image capture systems, having other configurations, may be used.

Preferably, located outside the patient's body in one or more locations, are an image receiver 12, preferably including an antenna or antenna array, an image receiver storage unit 16, a data processor 14, a data processor storage unit 19, and an image monitor 18, for displaying, inter alia, the images recorded by the capsule 40 and annotation information. Preferably, the image receiver 12 and image receiver storage unit 16 are small and portable, and are worn on the patient's body during recording of the images. Data processor storage unit 19 includes an image database 210 and an annotation database 200. Preferably, data processor 14, data processor storage unit 19 and monitor 18 are part of a personal computer or workstation which includes standard components such as processor 14, a memory, a disk drive, and input-output devices, although alternate configurations are possible, and the system and method of the present invention may be implemented on various suitable computing systems.

Data processor 14 may include any standard data processor, such as a microprocessor, multiprocessor, accelerator board, or any other serial or parallel high performance data processor. Image monitor 18 may be a computer screen, a conventional video display, or any other device capable of providing image or other data.

Preferably, the imager 46 is a suitable CMOS camera, such as a "camera on a chip" type CMOS imager specified by Given Imaging Ltd. of Israel and designed by Photobit Corporation of California, USA. In alternate embodiments, the imager 46 may be another device, for example, a CCD. The illumination source 42 may be, for example, one or more light emitting diodes, or another suitable light source.

In operation, imager 46 captures images and sends data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 is sent to the data processor 14 or the data processor storage unit 19. For example, the image receiver storage unit 16 may be taken off the patient's body and connected to the personal computer or workstation which includes the data processor 14 and data processor storage unit 19 via a standard data link, e.g., a serial or parallel interface of known construction. The image data is then transferred from the image receiver storage unit 16 to the image database 210 within data processor storage unit 19. Data processor 14 may analyze the data and provide the analyzed data to the image monitor 18, where a health professional views the image data. Data processor 14 operates software (not shown) which, in conjunction with basic operating software such as an operating system and device drivers, controls the operation of data processor 14. Preferably, the software controlling data processor 14 includes code written in the C++ language and possibly additional languages, but may be implemented in a variety of known methods.

The image data collected and stored may be stored indefinitely, transferred to other locations, or manipulated or analyzed. A health professional may use the images to diagnose pathological conditions of the GI tract, and, in addition, the system may provide information about the location of these pathologies. While, using a system where the data processor storage unit 19 first collects data and then transfers data to the data processor 14, the image data is not viewed in real time, other configurations allow for real time viewing.

The image monitor 18 presents the image data, preferably in the form of still and moving pictures, and in addition may present other information. In an exemplary embodiment, such additional information may include, but is not limited to, absolute time elapsed for the current image being shown and summary information for annotations. Absolute time elapsed for the current image being shown may be, for example, the amount of time that elapsed between the moment the capsule 40 was first activated and the image receiver 12 started receiving transmission from the capsule 40 and the moment that the current image being displayed was captured. In other embodiments, time elapsed may be other measures, such as time elapsed from the start of a moving image to the current point In further embodiments measures such as number of frames elapsed may be used. In an exemplary embodiment, the various categories of information are displayed in windows. Multiple monitors may be used to display image and other data.

Preferably, the in vivo imager system collects a series of still images as it traverses the GI tract. The images may be later presented as, for example, a stream of images or a moving image of the traverse of the GI tract. The in vivo imager system may collect a large volume of data, as the capsule 40 may take several hours to traverse the GI tract, and may record images at a rate of, for example, two images every second, resulting in the recordation of thousands of images. The image recordation rate (or frame capture rate) may be varied.

Preferably, the image data recorded and transmitted by the capsule 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel is recorded by a one byte (i.e., 0–255) brightness value. Preferably, images are stored sequentially in data processor storage unit 19. The stored data is comprised of one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle etc.

Preferably, data processor storage unit 19 stores a series of images recorded by a capsule 40. The images the capsule 40 records as it moves through a patient's GI tract may be combined consecutively to form a moving image. This moving image may be displayed in a window on monitor 18. The moving image may be frozen to view one frame, speeded up, or reversed; sections may be skipped; or any other method for viewing an image may be applied to the moving image. While the following discussion relates to the case where data from a capsule 40 is stored for later use, the system and method of the present invention may be used with systems allowing for real time viewing of image data.

In an exemplary embodiment, the moving image is stored as a series of images in the image database 210, and annotations are stored in the annotation database 200. Image database 210 and annotation database 200 may be implemented in a variety of known manners. While, in an exemplary embodiment, image database 210 and annotation database 200 are stored in the same general storage unit, in alternate embodiments image database 210 and annotation database 200 may be stored separately. Furthermore, the information stored in image database 210 and annotation database 200 may be stored in various combinations; for example, image and annotation information may be stored in the same database.

In an exemplary embodiment, the user may annotate portions of the moving image. When used herein, a "portion" of a moving image may include a single still image, a set of still images, or a series of still images which may be displayed as a moving image. When used herein, "annotation" and its derivatives may indicate any additional item of information or data added to or linked to a moving image or a portion of a moving image. For example, an annotation may include, but is not limited to, a textual, audio, or other note which is associated with a portion of a moving image, a bookmark, tab or label which is associated with a portion of a moving image, or a medical diagnosis or description of the portion.

A bookmark may be, for example, an indication or marker, or an index entry, which indicates to a user a portion of the moving image which is of interest. For example, a user may bookmark a frame which depicts a pathology in a GI tract. An annotation may be useful in a system where a large number of image frames are stored, only a certain number of which are relevant to a diagnosis. The user may store the image sequence and use the annotations to find the relevant portions and to record significant facts about those portions. When wishing to find portions of the moving image which are of interest, the user, or other users, may refer to the bookmarks or annotations.

In an exemplary embodiment, an annotation includes or refers to sets of images (which may include only one image), a time marking the time elapsed for the image (or the earliest of the set of images), and text. In an alternate embodiment the time may be replaced with another suitable measure, such as frames elapsed, etc. Each image may be either an actual image, stored in a known format, or may be a link to an image in the image file. In alternate embodiments, an annotation may include other combinations of information, including, for example, data in a non-textual format. Preferably, the annotations associated with a moving image may be exported from the system or saved as a file, and reports summarizing or otherwise organizing information in the annotations may be generated.

When viewing the moving image, the user is preferably presented with three windows on monitor 18. An image window provides the moving image, or still portions of that image. Such a window may include buttons or other controls which may alter the display of the image; for example, stop, play, pause, capture image, step, fast-forward, rewind, or other controls. Such controls may be activated by, for example, a pointing device such as a mouse or trackball. A timeline window provides a timeline, an indication of the total time elapsed for the moving image, and may provide other information, such as the total time of the moving image and summaries of annotations. In an exemplary embodiment, the timeline may be a bar labeled with time units, having summaries of annotations visually attached to the timeline at portions which indicate the time elapsed for the portions associated with the annotations. The summaries of the annotations may be any indication identifying an annotation; for example, a title or the first few characters or words of text from the annotation.

An annotation window on monitor 18 displays summaries of stored annotations which a user may view. Preferably, each annotation summary is displayed as a group of items of information including an image from the moving image (or one of the set of images), possibly displayed in a size smaller than the images displayed in the image window (possibly as a "thumbnail"), the elapsed time for the image (the relative time, per the timeline, that the image was captured), and a text title. The text title may include, for example, the first several words or characters from the textual annotation, or alternatively may include other title information. A scrollbar or other device may allow a user to display certain of the annotations within the annotation window. Preferably, a summary of each annotation is included in the timeline window, with a visual indication of the elapsed time associated with the annotation.

Figure 2:
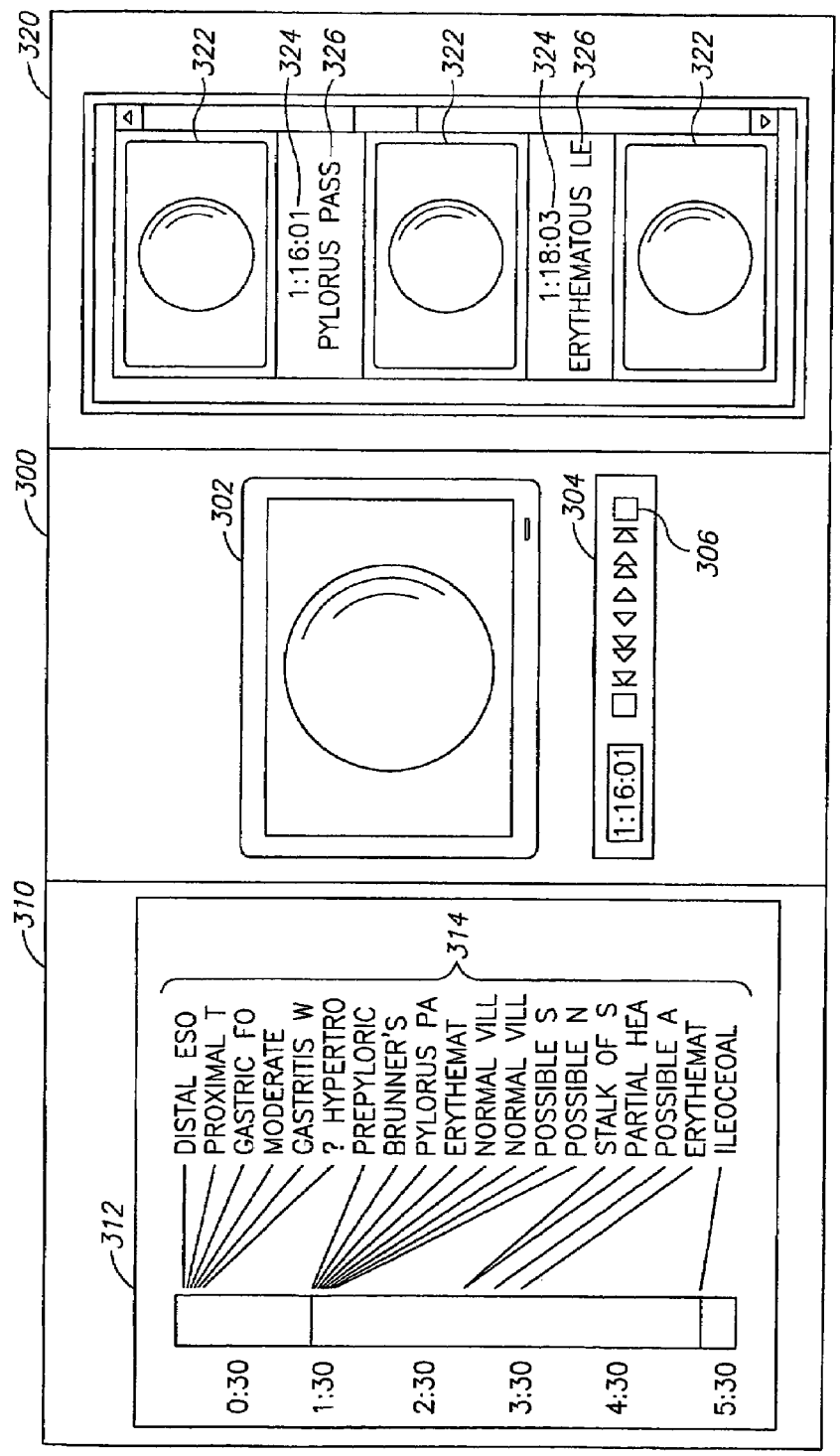
FIG. 2 is a representation of an image and a set of annotation summaries displayed on the monitor of FIG. 1, according to one embodiment of the present invention.

FIG. 2 is a representation of an image and a set of annotation summaries displayed on the monitor 18 of FIG. 1, according to one embodiment of the present invention. The image window 300 displays the moving image 302, or still portions of the moving image 302. Controls 304 may alter the display of the moving image 302. A capture image control 306 allows for the capture of an image from the moving image 302 and allows creation of an annotation. Timeline window 310 provides a timeline or time chart 312, and includes summaries 314 of annotations, connected to the appropriate relative time on the time chart 312. Annotation window 320 displays summaries of stored annotations. Preferably, each annotation includes at least one image 322, the elapsed time for the image 324, and a title 326. In the annotation window 320, each image 322 is preferably displayed in reduced form. In alternate embodiments, other information may be displayed, and information may be displayed in other sets of windows, and need not be displayed in windows.

Figure 3:
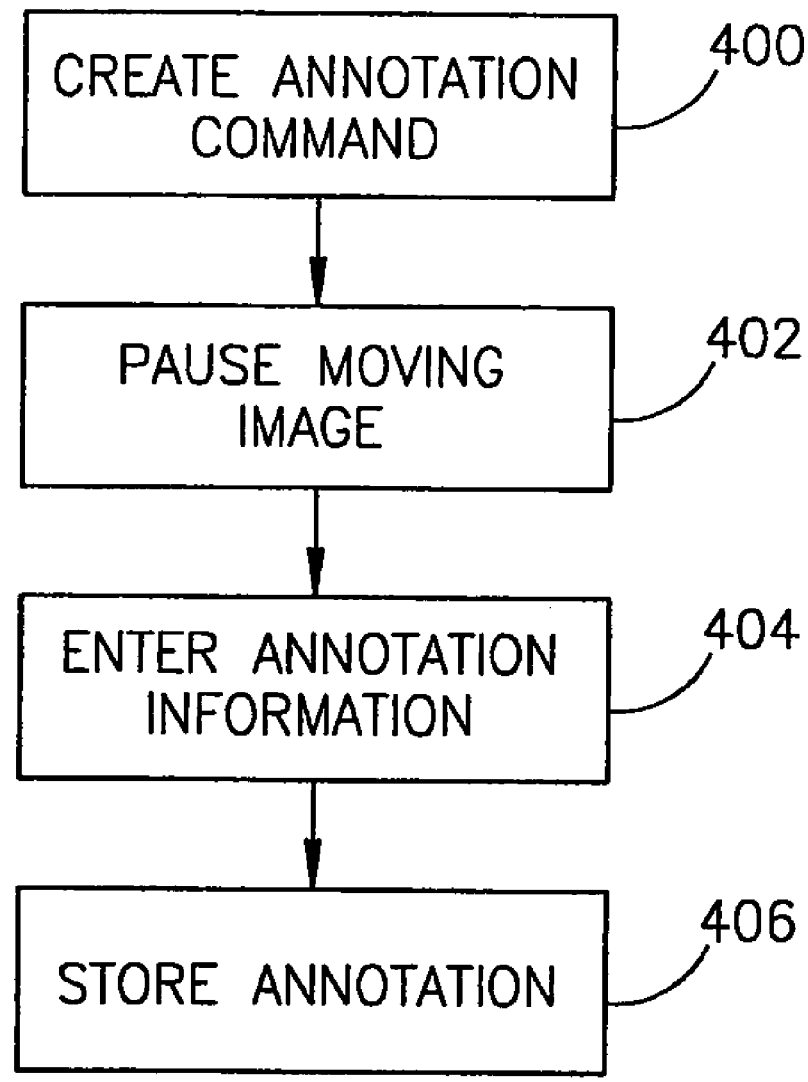
FIG. 3 depicts a flowchart for creating an annotation, according to one embodiment of the present invention.

While viewing a portion of the moving image, the user may create an annotation. FIG. 3 depicts a flowchart for creating an annotation, according to one embodiment of the present invention. In step 400, the user provides a command to the system to create an annotation. Preferably, the user presses a control, such as the capture image button 306. In step 402, if the moving image is not yet paused, the moving image is paused, and the still image viewed is marked or set aside, and possibly displayed in the annotation window 320. In step 404, the user enters annotation information, such as a textual description of the image using, for example, a keyboard. In step 406, the annotation is stored in an entry in the annotation database 200. Preferably, the entry in the annotation database 200 corresponding to the annotated image in the image database 210 includes a link, such as a pointer or a database reference, to the image in the image database 210 or to a database record corresponding to the image. The link may include, for example, the relative time the image was captured or an image frame number. In alternate embodiments sets or series of images may be stored in an annotation. In further embodiments, no such links are needed, as the image data and annotation data may be stored in the same database. In alternate embodiments other series of steps may be used to carry out the present invention. In further embodiments, annotations may be entered by capturing information in various media, such as vocal comments (via, for example, a microphone) or links of other data.

A user may view and edit an annotation. Typically, a user first selects the annotation by, for example, using a pointing device to indicate the annotation in the timeline window or the annotation window. Annotations or annotation summaries may appear in areas other than a timeline or annotation window. The full text or representation of the annotation appears or is otherwise displayed or output, and the user may, for example, read or edit the text, for example in a pop-up window. The user may see an enlarged view of the image or set of images included in the annotation. If the annotation includes a set of images, the user may view the set of images as a moving image.

In an alternate embodiment, annotations may be created in conjunction with or based on analysis performed by the data processor 14 or the imaging system. For example, in a system where images captured by a capsule similar to capsule 40 are analyzed for, for example, low motility or for blood in the GI tract, an annotation may automatically be created when such conditions are seen. Thus, the user may access a set of bookmarks which refer the user to the portions of the moving image where such conditions exist.

It will be appreciated by persons skilled in the art that the present invention is not limited by what has been particularly shown and described hereinabove.

The invention claimed is:

1. A method for annotating an image stream, the method comprising:
   accepting images acquired by a swallowable capsule directly capturing the images while traversing a body lumen;
   creating a stream of images;
   displaying the images on a monitor in the form of the stream of images;
   accepting an annotation from a user, the annotation corresponding to one or more frames within the stream of images;
   recording the annotation in a database;
   associating the annotation with one or more frames within the stream of images thereby creating an annotated image;
   displaying to a user a time chart of the stream of images; and
   displaying to the user annotation summaries corresponding to times on the time chart, and displaying for each annotated image at least one thumbnail image of said annotated image.

2. The method of claim 1, wherein one or more frames within the stream of images comprises a single image.

3. The method of claim 1, wherein one or more frames within the stream of images comprises a subset of the stream of images.

4. The method of claim 1, wherein the step of accepting the annotation includes at least the step of accepting a text comment.

5. The method of claim 1, wherein the step of accepting the annotation includes at least the step of marking a portion of the stream of images.

6. The method as in claim 1 wherein the images are images from a gastrointestinal tract.

7. The method as in claim 1, wherein the step of accepting the annotation includes at least the steps of:
   accepting a create annotation command from a user;
   marking a set of frames of the stream of images;
   accepting text from the user; and
   storing the text in a record associated with the set of frames.

8. The method as in claim 1, further comprising:
   accepting from a user an indication of an annotation to view; and
   displaying the annotation and said one or more frames within the stream of images corresponding to said annotation.

9. A method for displaying images captured by a swallowable capsule, the method comprising:
   forming a moving stream of images from a plurality of images captured by a swallowable capsule traversing a body lumen;
   after said step of forming, displaying the moving stream of images;
   selecting at least one image from said stream of images to form at least an annotated image; and
   displaying said at least one annotated image together with an annotation wherein said annotation comprises at least one thumbnail image of said annotated image.

10. The method of claim 9, wherein the at least one image within the stream of images comprises a subset of the stream of images.

11. The method of claim 9, wherein the annotation includes at least a text comment.

12. The method of claim 9, wherein the step of annotating includes at least the step of marking a portion of the stream of images.

13. The method as in claim 9, wherein the images are images from a gastrointestinal tract.

14. The method as in claim 9, wherein the step of annotating includes at least the steps of:
   accepting a create annotation command from a user;
   marking a set of frames of the stream of images;
   accepting text from the user; and
   storing the text in a record associated with the set of frames.

15. The method as in claim 9, comprising:
   displaying to a user a time chart of the stream of images; and
   displaying to the user annotation summaries corresponding to times on the time chart.

16. A system for displaying images, comprising:
   a swallowable capsule to capture a plurality of images;
   a controller to:
      form a moving stream of images from the images captured;
      after forming the moving stream of images, display the moving stream of images;
      select at least one image from the stream of images;
      annotate said at least one image to form an annotated image; and
      display said annotated image together with an annotation, wherein said annotation comprises at least one thumbnail image of said annotated image.

17. The system of claim 16, comprising a set of links linking each annotation with a subset of the images.

18. The system of claim 16, wherein each annotation includes at least a text comment.

19. The system of claim 16, wherein each annotation includes at least a marker.

20. The system of claim 16, wherein the images are images from a gastrointestinal tract.

* * * * *